United States Patent [19]
Granados

[11] Patent Number: 5,717,069
[45] Date of Patent: Feb. 10, 1998

[54] DNA SEQUENCE CODING FOR ENHANCIN POLYPEPTIDE WHICH ENHANCES VIRUS INFECTION OF HOST INSECTS

[75] Inventor: Robert R. Granados, Ithaca, N.Y.

[73] Assignee: Boyce Thompson Institute for Plant Research, Inc., Ithaca, N.Y.

[21] Appl. No.: 701,846

[22] Filed: Aug. 23, 1996

Related U.S. Application Data

[60] Provisional application No. 60/002,743, Aug. 24, 1995.

[51] Int. Cl.$^6$ ............... C07K 1/00; C12N 15/00; C12P 21/06; A61K 39/12
[52] U.S. Cl. ............... 530/350; 530/826; 530/825; 435/69.1; 435/240.1; 435/235.1; 435/320.1; 424/199.1; 424/204.1
[58] Field of Search ............... 435/69.1, 240.1, 435/235.1, 320.1; 424/199.1, 204.1; 530/350, 826, 825

[56] References Cited

U.S. PATENT DOCUMENTS

| | | | |
|---|---|---|---|
| 4,904,645 | 2/1990 | Puritch et al. | 514/65 |
| 4,973,667 | 11/1990 | Granados | 530/350 |
| 5,011,685 | 4/1991 | Granados | 424/93 |
| 5,475,090 | 12/1995 | Granados et al. | 530/350 |

OTHER PUBLICATIONS

Hoshimoto et al, 1991, J. Gen. Virology, v. 72 pp. 2645–2651.
Roelvink, P.W. et al, 1995, Characterization of the *Helicoverpa armigera* and *Pseudaletia unipuncta* granulovirus enhancing genes, Jnl. Of Gen. Virology, 76: 2693–2705.
Hamm, J.J., 1982, Extension of the Host Range for a Granulosis Virus from *Heliothis armiger* from South Africa, Environmental Entomology, vol. II, No. 1, pp. 159–160.
Derksen, A.C. et al, 1988, Alteration of a Lepidopteran Peritrophic Membrane by Baculoviruses and Enhancement of Viral Infectivity, Virology, 167:242–250.
Tanada, Y., et al, 1975, Enzyme synergistic for insect viruses, Nature, Nol. 254:328–329.
Tanada, Y, et al, 1985, A Synopsis of Studies on the Synergistic Property of an Insect Baculovirus: A Tribute to Edward A. Steinhaus, Jnl. Of Invert. Pathology, 45: 125–138.

Tanada, Y., et al, 1959, Synergism between Two Viruses of the Armyworm, *Pseudalertia unipuncta* (Haworth) (Lepidoptera, Noctuidae)[1], Jnl. Of Insect Pathology 1:215–231.

Blissard, G.W. et al, 1990, Baculovirus Diversity and Molecular Biology, Annu. Rev. Entomo., 35:125–125.

Wood, H.A. et al, 1991, Genetically Engineered Baculoviruses as Agents For Pest Control, Annu. Rev. Microbiol., 45:69–87.

Corsaro, B. Et al, Baculovirus Enhancing Proteins as Determinants of Viral Pathogenesis, Paraasites and Pathogens of Insects, vol. 2, pp. 127–145.

Miller. L.K. 1988, Baculoviruses as Gene Expression Vectors, Ann. Rev. Microbiol. 42: 177–99.

Westwood, J. Et al, 1993, Analyses of Alternative Poly (A) Signals for Use in Baculovirus Expression Vectors, Virology 195, 90–99.

Gallo, L.G. et al, 1994, In Vivo Enhancement of Baculovirus Infection by the Viral Enhancing Factor of a Granulosis Virus of the Cabbage Looper, *Trichoplusis ni* (Lepidopters: Noctuidae), Jnl. Of Invertebrate Pathology 58, 203–210.

*Primary Examiner*—Marian C. Knode
*Assistant Examiner*—Ali R. Salimi
*Attorney, Agent, or Firm*—Brown, Pinnisi & Michaels

[57] ABSTRACT

This disclosure relates to an isolated and cloned DNA from a granulovirus virus which comprises an amino acid sequence of the vital gene encoding a polypeptide isolated from occlusion bodies of certain baculoviruses and which polypeptide possesses the biological activity of enhancing baculovirus infectivity. Such proteins termed herein as "enhancins" are found within the viral occlusion body, have a disruptive effect on the insect peritrophic membrane (PM) proteins, and/or interact with the midgut epithelium in such a manner as to permit the increased adsorption, penetration and uptake of virus particles by midgut cells with a concomitant increase in host mortality. Disclosed herein is a recombinant DNA sequence which codes for the enhancin protein of the *Helicoverpa armigera* granulovirus virus. The DNA sequence is shown in SEQ. ID. NO.: 1 and the open reading frame is shown in SEQ. ID. NO.: 1: base pairs 271–2976. The amino acid sequence of the enhancin protein is shown in SEQ. ID. NO.: 2.

14 Claims, 2 Drawing Sheets

FIGURE 1a

```
              1                                                                    60
PsunGV-H   MSYKVIVPATVLPPWLRVGE NWIFARHRRTEVGVVLPANT KFRVRADFSRAGFTRPVIVR
TnGV       MSYKVIVPATVLPPWLRVGE NWIFARHRRTEVGVVLPANT KFRVRADFSRAGFTRPVIVR
HearGV     MSYNVIVPTTVLPPWLRIGQ NWIFARHRRTEVGVVLPANT KFRVRADFAKWGITRPVIVR
Consensus  *** **** ******** *  ******************* *******  * *******

61                                                                  120
PsunGV-H   LLNNNRNTEREINLNNDQWM EVEHAHESVPFVDWPVGERN IMAEVYFEIDGPHIPLPVYV
TnGV       LLNNNRSTEREINLNNDQWM EVEHAHESVPFVDWLVGEKN TMAEVYFEIDGPHIPLPVYV
HearGV     LLNNNRNTEREINLTNDQWI EMEHEHECVPFVDWPVGEKN TMAEVHFEIDGPHIPLPVYV
Consensus  ****** ******* **** * ** ** ****** *** *  **** ****************

121                                                                 180
PsunGV-H   FNTRPVEHFKSEYRQSSSGY CFLYLDLVCMLVPPASKNAL LDVNIFELHQFYNEIINYYD
TnGV       FNTRPVEHFKSEYRQSSSGY CFLYLDLVCMLVPPASKNAL LDVNIFELHQFYNEIINYYD
HearGV     FNTRPVENFKSEYRQSSSGY CFLYLDLVCILVPPASKNVL LDTDLFELHQFYNEIINYYD
Consensus  ******* ************ ********* ******** * **  **************

181                                                                 240
PsunGV-H   DLCGLVEDPYADTVDSNLPN KAAFVKADAGGPGGAYYGPF WTAPASSNLGDYLRISPTNW
TnGV       DLCGLVEDPYADTVDSNLPN KAAFVKADAGGPGGAYYGPF WTAPASSNLGDYLRISPTNW
HearGV     DLCGLVEDPYADTVDSNLPN KAAFVKADGGGPGGAYYGAF WTAPASTNLGEYLRVSPTNW
Consensus  ******************** ******** *********  * ****** *** *** *****

241                                                                 300
PsunGV-H   MVIHELGHAYDFVFTVNTIL IEIWNNSLCDRIQYKWMNKT KRQQLARVYENRRPQKEATI
TnGV       MVIHELGHAYDFVFTVNTIL IEIWNNSLCDRIQYKWMNKI KRQQLARVYENRRPQKEATI
HearGV     MVIHELGHAYDFVFTVNTRL IEIWNNSFCDRIQYTWMNKT KRQQLARIYENQRPQKEAAI
Consensus  ****************** * ******* ****** **** *  ****** *** ****** *

301                                                                 360
PsunGV-H   QALIDNNSPFDNWGFFERLI IFTWLYNPQRGLDTLRNINH SYRVHATRNSSIPYPQIWSW
TnGV       QALIDNNSPFDNWGFFERLI IFTWLYNPQRGLDTLRNINH SYRVHATRNSSIPYPQIWSW
HearGV     QALIDNNVPFDNWDFFEKLS IFAWLYNPQRGLDTLRNINH SYRLHAARNPVTPYPQIWAW
Consensus  ******* ***** *** *  ** **************** *** **  **     ****** *

361                                                                 420
PsunGV-H   LTTSAYDNFWLYFNLVGVYP ADFYVNEHNKVVHFNLHLRA LALGQSVRYPIKYIITDFDL
TnGV       LTTSAYDNFWLYFNLVGVYP ADFYVNEHNKVVHFNLHLRA LALGQSVRYPIKYIITDFDL
HearGV     LMSCGYDNFWLYFNRIGLYP ADFYINEHNKVVHFNLHMRA LALGQSVRYPIKYIITDFDL
Consensus  *  ******** *  ** *** ****  ************ ** ********************

421                                                                 480
PsunGV-H   VSKNYDIKQYLESNFDLVIP EELRQTDLLADVRVVCVIDD PSQIVGEPFSVYDGNERVFE
TnGV       VSKNYDIKQYLESNFDLVIP EELRQTDLLADVRVVCVIDD PSQIVGEPFSVYDGNERVFE
HearGV     LQKNYDIKQYLESNFDLVIP EELRQTDLVADVRVVCVIDD PSQIIGEPFSLYDGNERVFE
Consensus    **************** ******** ************ **** ***** *********

481                                                                 540
PsunGV-H   STVATDGNMYLVGVGPGVYT LRAPRGKNKRYKLHLAHSPR EPVHPANDHMYLLVTYPYYN
TnGV       STVATDGNMYLVGVGPGVYT LRAPRGKNKRYKLHLAHSPR EPVHPANDHMYLLVTYPYYN
HearGV     STVATDGNMYLVGVGPGVYT LRAPRGKDKRYKLHLAHSPN EPVHPANDHMYLLVTYPYYN
Consensus  ******************** ******* ************ ********************

541                                                                 600
PsunGV-H   QTLTYTPYVNSDLAVDMAHL FGSNDRRYVATIYFNPFEQT VTVHLNNIRAGRENNTTLYF
TnGV       QTLTYTPYVNSDLAVDMAHL FGSNDRRYVATIYFNPFEQT VTVHLNNIRAGRENNTTLYF
HearGV     QTLTYTRYITSDLAIDAAHL FGT.DRLYVATIYFDALQQT VTVYLNNIRTGRENNTTLYF
Consensus  ****** * **** * *** ** ** ****** * ** ** *** *********
```

FIGURE 1b

```
              601                                                            660
PsunGV-H      EMVISNPFNGQSQTFTILED  NPTLRQGYYKFDVVTYSSIR  LNMSVAGRLLFGDTFLPEGT
TnGV          EMVISNPFNGQSQTFTILED  NPTLRQGYYKFDVVTYSSIR  LNMSVAGRLLFRRYIFAGGT
HearGV        EMEIHNPFIGTSSKFTLLED  NVTMRQGYYKFPAVTFSSIR  LHIRDDNRLMLVDKYLPAGD
Consensus     ** * *** * *  ** ***  * * *******  ** ****  *         **           *

661                                                            720
PsunGV-H      TTLTMFPNQVLEPNLFPDGS  ALNRTLARLREQAAFLDNYS  QLMYIENELRDSIYLASQLV
TnGV          TTLTMFPNQVLEPNLFPDGS  ALNRTLARLREQAAFLDNYS  QLMYIENELRDTIYLASQLV
HearGV        TLLFMFPNQIVDNNIFPDGS  ILTSTYNRIKEQAAFIENHK  QLLYIENELRDSIYLASQFV
Consensus     * * *****    * *****  *   *   *  ****  *     ** ********* ****** *

721                                                            780
PsunGV-H      DPASDEFVKYYPDYFRDPHT  YVYLFRFRGLGDFVLLDLQI  VPLLNLATVRIANNHNGPHS
TnGV          DPASDEFVKYYPDYFRDPHT  YVYLFRFRGLGDFVLLDLQI  VPLLNLATVRIANIQNGPHS
HearGV        NSDSNEFLKYFPDYFRDPHT  FSYLFRFRGLGDFMLLELQI  VPILNLASVRVGNHHGPHS
Consensus       ** ** ** ********   ************ ** ***  ** ****  *   *  *****

781                                                            840
PsunGV-H      YFDTLYFKVELRDTNGAIVF  SYSRRGNEPMTPEHHKFEVY  SGYTVELFMREPGNRLQLIV
TnGV          YFDTLYFKVELRDTNGAIVF  SYSRRGNEPMTPEHHKFEVY  SGYTVELFMREPGNRLQLIV
HearGV        YFNTTYLSVEVRDTSGGVVF  SYSRLGNEPMTHEHHKFEVF  KDYTIHLFIQEPGQRLQLIV
Consensus     ** *  * ** *** * *  **  **** ****** ******   **   **   *** ******

841                                                            900
PsunGV-H      NKMLDTALPSTQNIFARITD  TQLVVGDTSI.....EDNLV  TSINVDCGDDDNQKIRVVET
TnGV          NKMLDTALPSTQNIFARITD  TQLVVGDTSI.....EDNLV  TSINVDCGDDDNQKIRVVET
HearGV        NKTLDTALPNSQNIYARLTA  TQLVVGEQSIIISDDNDFVP  PPPRVNCGD...QQIRVVET
Consensus     ** ****** ** ***   * ******  **         *        * ***    * ******

901
PsunGV-H      LKMIAF
TnGV          LKMIAF
HearGV        LKMIAF
Consensus     ******
```

5,717,069

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 3186 base pairs
( B ) TYPE: nucleic acid
( C ) STRANDEDNESS: double
( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Helicoverpa armigera granulosis virus ( i x ) FEATURE:
( A ) NAME/KEY: CDS
( B ) LOCATION: 271..2976

( x i ) SEQUENCE DESCRIPTION: SEQ ID NO:1:

```
CTATATGTGG TAAGATTGAT TGAATGTTCG TTTGCTCTCG CGTTGTTTAA AAAACGCAAC      60

AAACACCGGT ATTAGCGGAG CGGTCTCCTG TATCCGGCAG CGGACTGTCG CGTTAGCGTG     120

CACCACTACG CCGGCCGGAA CGCGACCGTG TTTGAGCGCC AACCAATTGT CCTGTGGCCT     180

CAAATAAGGC GGCACTGCTA AAGATGGTAC CGGTAGAATA ATGGAAGTTT TGTTCTTTCA     240

CACAACATTA CGCTGTCTTA AATTAAGATT ATG TCG TAC AAC GTA ATT GTG CCT      294
                                 Met Ser Tyr Asn Val Ile Val Pro
                                  1               5

ACT ACC GTG CTG CCG CCG TGG CTG AGG ATC GGT CAA AAT TGG ATA TTC      342
Thr Thr Val Leu Pro Pro Trp Leu Arg Ile Gly Gln Asn Trp Ile Phe
     10                  15                  20

GCT AGA CAC AGA CGC ACC GAA GTC GGT GTG GTG TTA CCT GCA AAC ACA      390
Ala Arg His Arg Arg Thr Glu Val Gly Val Val Leu Pro Ala Asn Thr
 25                  30                  35                  40

AAG TTT CGG GTT CGA GCC GAT TTC GCT AAA TGG GGC ATC ACG AGG CCC      438
Lys Phe Arg Val Arg Ala Asp Phe Ala Lys Trp Gly Ile Thr Arg Pro
                 45                  50                  55

GTG ATC GTG CGC CTC TTG AAC AAC AAC CGT AAC ACC GAG CGC GAG ATA      486
Val Ile Val Arg Leu Leu Asn Asn Asn Arg Asn Thr Glu Arg Glu Ile
             60                  65                  70

AAT TTA ACC AAC GAC CAA TGG ATA GAG ATG GAG CAC GAG CAC GAG TGT      534
Asn Leu Thr Asn Asp Gln Trp Ile Glu Met Glu His Glu His Glu Cys
         75                  80                  85

GTG CCG TTC GTC GAC TGG CCG GTG GGT GAA AAA AAC ACC ATG GCC GAG      582
Val Pro Phe Val Asp Trp Pro Val Gly Glu Lys Asn Thr Met Ala Glu
     90                  95                 100

GTA CAC TTT GAA ATC GAC GGA CCA CAC ATA CCG CTT CCC GTG TAC GTG      630
Val His Phe Glu Ile Asp Gly Pro His Ile Pro Leu Pro Val Tyr Val
105                 110                 115                 120

TTC AAC ACG AGA CCC GTG GAA AAC TTT AAG AGC GAG TAC CGC CAG AGT      678
Phe Asn Thr Arg Pro Val Glu Asn Phe Lys Ser Glu Tyr Arg Gln Ser
                125                 130                 135

TCG TCG GGC TAC TGC TTC CTG TAT TTG GAC CTG GTG TGT ATT TTG GTG      726
Ser Ser Gly Tyr Cys Phe Leu Tyr Leu Asp Leu Val Cys Ile Leu Val
            140                 145                 150

CCG CCG GCT AGT AAA AAC GTG TTA CTA GAC ACG GAC CTG TTT GAG CTC      774
```

| | | | | | | | | | | | | | | | |
|---|---|---|---|---|---|---|---|---|---|---|---|---|---|---|---|
| Pro | Pro | Ala | Ser | Lys | Asn | Val | Leu | Leu | Asp | Thr | Asp | Leu | Phe | Glu | Leu |
| | | | 155 | | | 160 | | | | | | 165 | | | |

```
CAT CAA TTT TAT AAC GAA ATT ATT AAT TAC TAT GAC GAT TTG TGC GGT     822
His Gln Phe Tyr Asn Glu Ile Ile Asn Tyr Tyr Asp Asp Leu Cys Gly
    170             175                 180

TTG GTC GAG GAC CCG TAC GCA GAC ACT GTG GAT TCA AAC CTA CCC AAC     870
Leu Val Glu Asp Pro Tyr Ala Asp Thr Val Asp Ser Asn Leu Pro Asn
185             190                 195                 200

AAG GCG GCA TTC GTG AAA GCC GAC GGT GGT GGT CCC GGC GGT GCT TAT     918
Lys Ala Ala Phe Val Lys Ala Asp Gly Gly Gly Pro Gly Gly Ala Tyr
                205                 210                 215

TAC GGG GCA TTC TGG ACG GCT CCC GCC AGC ACA AAT CTA GGC GAA TAT     966
Tyr Gly Ala Phe Trp Thr Ala Pro Ala Ser Thr Asn Leu Gly Glu Tyr
            220                 225                 230

CTC CGG GTG TCG CCC ACC AAT TGG ATG GTT ATT CAC GAG CTG GGT CAC    1014
Leu Arg Val Ser Pro Thr Asn Trp Met Val Ile His Glu Leu Gly His
        235                 240                 245

GCG TAC GAT TTC GTG TTT ACT GTG AAC ACT CGC CTT ATA GAA ATC TGG    1062
Ala Tyr Asp Phe Val Phe Thr Val Asn Thr Arg Leu Ile Glu Ile Trp
    250                 255                 260

AAC AAC TCG TTC TGC GAT CGG ATA CAA TAC ACG TGG ATG AAC AAA ACC    1110
Asn Asn Ser Phe Cys Asp Arg Ile Gln Tyr Thr Trp Met Asn Lys Thr
265                 270                 275                 280

AAG CGA CAG CAA CTG GCT CGC ATT TAC GAG AAC CAA CGA CCC CAG AAG    1158
Lys Arg Gln Gln Leu Ala Arg Ile Tyr Glu Asn Gln Arg Pro Gln Lys
                285                 290                 295

GAG GCG GCT ATT CAA GCG CTA ATC GAC AAC AAT GTA CCG TTT GAT AAT    1206
Glu Ala Ala Ile Gln Ala Leu Ile Asp Asn Asn Val Pro Phe Asp Asn
            300                 305                 310

TGG GAT TTT TTT GAG AAA CTC AGC ATT TTT GCA TGG CTG TAC AAT CCG    1254
Trp Asp Phe Phe Glu Lys Leu Ser Ile Phe Ala Trp Leu Tyr Asn Pro
        315                 320                 325

CAA AGG GGA CTG GAC ACT TTG CGT AAT ATC AAT CAT TCG TAC AGG TTG    1302
Gln Arg Gly Leu Asp Thr Leu Arg Asn Ile Asn His Ser Tyr Arg Leu
    330                 335                 340

CAC GCT GCC CGC AAT CCA GTT ACG CCA TAC CCG CAA ATT TGG GCA TGG    1350
His Ala Ala Arg Asn Pro Val Thr Pro Tyr Pro Gln Ile Trp Ala Trp
345                 350                 355                 360

TTG ATG AGT TGT GGT TAC GAC AAC TTT TGG TTG TAC TTT AAT CGA ATA    1398
Leu Met Ser Cys Gly Tyr Asp Asn Phe Trp Leu Tyr Phe Asn Arg Ile
                365                 370                 375

GGT TTG TAC CCT GCC GAT TTT TAC ATT AAC GAA CAC AAT AAA GTC GTG    1446
Gly Leu Tyr Pro Ala Asp Phe Tyr Ile Asn Glu His Asn Lys Val Val
            380                 385                 390

CAT TTC AAT CTG CAC ATG CGC GCC TTA GCG CTG GGA CAG AGT GTG CGT    1494
His Phe Asn Leu His Met Arg Ala Leu Ala Leu Gly Gln Ser Val Arg
        395                 400                 405

TAC CCT ATC AAA TAT ATT ATT ACC GAC TTT GAT TTA TTG CAA AAG AAC    1542
Tyr Pro Ile Lys Tyr Ile Ile Thr Asp Phe Asp Leu Leu Gln Lys Asn
    410                 415                 420

TAC GAC ATA AAG CAA TAT TTA GAG AGT AAC TTT GAT CTT GTA ATA CCG    1590
Tyr Asp Ile Lys Gln Tyr Leu Glu Ser Asn Phe Asp Leu Val Ile Pro
425                 430                 435                 440

GAA GAG TTG AGA CAG ACC GAT CTG GTT GCG GAC GTA CGA GTG GTG TGC    1638
Glu Glu Leu Arg Gln Thr Asp Leu Val Ala Asp Val Arg Val Val Cys
                445                 450                 455

GTC ATC GAC GAC CCA TCA CAA ATT ATA GGT GAA CCG TTT AGT TTG TAC    1686
Val Ile Asp Asp Pro Ser Gln Ile Ile Gly Glu Pro Phe Ser Leu Tyr
            460                 465                 470

GAC GGT AAC GAA CGA GTT TTT GAG AGC ACA GTA GCC ACG GAT GGT AAC    1734
```

-continued

| | | | | | | | | | | | | | | | |
|---|---|---|---|---|---|---|---|---|---|---|---|---|---|---|---|
| Asp | Gly | Asn 475 | Glu | Arg | Val | Phe | Glu 480 | Ser | Thr | Val | Ala | Thr 485 | Asp | Gly | Asn |

| ATG | TAT | TTA | GTT | GGC | GTG | GGT | CCG | GGA | GTG | TAC | ACT | CTA | CGC | GCG | CCC | 1782 |
|---|---|---|---|---|---|---|---|---|---|---|---|---|---|---|---|---|
| Met | Tyr 490 | Leu | Val | Gly | Val | Gly | Pro 495 | Gly | Val | Tyr | Thr | Leu 500 | Arg | Ala | Pro | |

| CGC | GGC | AAA | GAC | AAA | CGC | TAC | AAA | CTC | CAC | TTG | GCA | CAC | TCG | CCC | AAC | 1830 |
|---|---|---|---|---|---|---|---|---|---|---|---|---|---|---|---|---|
| Arg 505 | Gly | Lys | Asp | Lys | Arg 510 | Tyr | Lys | Leu | His 515 | Leu | Ala | His | Ser | Pro 520 | Asn | |

| GAG | CCG | GTT | CAT | CCG | GCT | AAC | GAT | CAC | ATG | TAT | CTA | CTC | GTG | ACA | TAT | 1878 |
|---|---|---|---|---|---|---|---|---|---|---|---|---|---|---|---|---|
| Glu | Pro | Val | His | Pro 525 | Ala | Asn | Asp | His | Met 530 | Tyr | Leu | Leu | Val | Thr 535 | Tyr | |

| CCA | TAT | TAC | AAT | CAA | ACG | TTA | ACC | TAC | ACA | CGA | TAT | ATA | ACT | TCG | GAC | 1926 |
|---|---|---|---|---|---|---|---|---|---|---|---|---|---|---|---|---|
| Pro | Tyr | Tyr | Asn 540 | Gln | Thr | Leu | Thr | Tyr 545 | Thr | Arg | Tyr | Ile | Thr 550 | Ser | Asp | |

| CTT | GCA | ATA | GAC | GCG | GCC | CAC | TTA | TTC | GGT | ACC | GAC | CGC | TTG | TAT | GTG | 1974 |
|---|---|---|---|---|---|---|---|---|---|---|---|---|---|---|---|---|
| Leu | Ala | Ile | Asp 555 | Ala | Ala | His | Leu | Phe 560 | Gly | Thr | Asp | Arg 565 | Leu | Tyr | Val | |

| GCC | ACG | ATA | TAT | TTC | GAC | GCA | TTA | CAG | CAG | ACT | GTG | ACC | GTG | TAT | CTG | 2022 |
|---|---|---|---|---|---|---|---|---|---|---|---|---|---|---|---|---|
| Ala | Thr 570 | Ile | Tyr | Phe | Asp | Ala 575 | Leu | Gln | Gln | Thr | Val 580 | Thr | Val | Tyr | Leu | |

| AAC | AAT | ATT | CGC | ACT | GGC | AGG | GAA | AAC | AAC | ACC | ACC | TTG | TAT | TTT | GAA | 2070 |
|---|---|---|---|---|---|---|---|---|---|---|---|---|---|---|---|---|
| Asn 585 | Asn | Ile | Arg | Thr | Gly 590 | Arg | Glu | Asn | Asn | Thr 595 | Thr | Leu | Tyr | Phe | Glu 600 | |

| ATG | GAA | ATA | CAT | AAT | CCG | TTT | ATT | GGC | ACT | TCT | TCG | AAA | TTT | ACT | TTG | 2118 |
|---|---|---|---|---|---|---|---|---|---|---|---|---|---|---|---|---|
| Met | Glu | Ile | His | Asn 605 | Pro | Phe | Ile | Gly | Thr 610 | Ser | Ser | Lys | Phe | Thr 615 | Leu | |

| TTA | GAG | GAT | AAC | GTC | ACG | ATG | CGC | CAG | GGA | TAT | TAT | AAA | TTT | CCG | GCG | 2166 |
|---|---|---|---|---|---|---|---|---|---|---|---|---|---|---|---|---|
| Leu | Glu | Asp | Asn 620 | Val | Thr | Met | Arg | Gln 625 | Gly | Tyr | Tyr | Lys | Phe 630 | Pro | Ala | |

| GTC | ACC | TTT | AGC | TCG | ATT | CGT | TTA | CAC | ATA | AGA | GAT | GAC | AAC | AGA | CTA | 2214 |
|---|---|---|---|---|---|---|---|---|---|---|---|---|---|---|---|---|
| Val | Thr | Phe 635 | Ser | Ser | Ile | Arg | Leu 640 | His | Ile | Arg | Asp | Asp 645 | Asn | Arg | Leu | |

| ATG | CTG | GTA | GAT | AAA | TAT | TTA | CCA | GCG | GGC | GAC | ACG | TTG | CTG | TTC | ATG | 2262 |
|---|---|---|---|---|---|---|---|---|---|---|---|---|---|---|---|---|
| Met | Leu | Val 650 | Asp | Lys | Tyr | Leu | Pro 655 | Ala | Gly | Asp | Thr 660 | Leu | Leu | Phe | Met | |

| TTT | CCC | AAT | CAA | ATC | GTT | GAC | AAT | AAT | ATA | TTT | CCC | GAT | GGG | TCA | ATA | 2310 |
|---|---|---|---|---|---|---|---|---|---|---|---|---|---|---|---|---|
| Phe 665 | Pro | Asn | Gln | Ile | Val 670 | Asp | Asn | Asn | Ile | Phe 675 | Pro | Asp | Gly | Ser | Ile 680 | |

| TTG | ACC | AGC | ACA | TAC | AAC | CGT | ATA | AAA | GAA | CAA | GCT | GCT | TTC | ATC | GAA | 2358 |
|---|---|---|---|---|---|---|---|---|---|---|---|---|---|---|---|---|
| Leu | Thr | Ser | Thr | Tyr 685 | Asn | Arg | Ile | Lys | Glu 690 | Gln | Ala | Ala | Phe | Ile 695 | Glu | |

| AAC | CAT | AAA | CAG | CTG | TTG | TAC | ATT | GAA | AAC | GAA | TTA | CGC | GAC | AGC | ATA | 2406 |
|---|---|---|---|---|---|---|---|---|---|---|---|---|---|---|---|---|
| Asn | His | Lys | Gln 700 | Leu | Leu | Tyr | Ile | Glu 705 | Asn | Glu | Leu | Arg | Asp 710 | Ser | Ile | |

| TAC | TTG | GCG | TCA | CAA | TTT | GTG | AAT | AGT | GAT | TCC | AAC | GAA | TTT | TTA | AAG | 2454 |
|---|---|---|---|---|---|---|---|---|---|---|---|---|---|---|---|---|
| Tyr | Leu | Ala 715 | Ser | Gln | Phe | Val | Asn 720 | Ser | Asp | Ser | Asn | Glu 725 | Phe | Leu | Lys | |

| TAT | TTT | CCT | GAT | TAT | TTT | AGA | GAC | CCT | CAT | ACG | TTC | TCA | TAC | CTG | TTT | 2502 |
|---|---|---|---|---|---|---|---|---|---|---|---|---|---|---|---|---|
| Tyr | Phe | Pro 730 | Asp | Tyr | Phe | Arg | Asp 735 | Pro | His | Thr | Phe 740 | Ser | Tyr | Leu | Phe | |

| CGG | TTC | AGA | GGC | TTG | GGT | GAT | TTC | ATG | TTG | CTA | GAA | TTA | CAA | ATT | GTG | 2550 |
|---|---|---|---|---|---|---|---|---|---|---|---|---|---|---|---|---|
| Arg 745 | Phe | Arg | Gly | Leu | Gly 750 | Asp | Phe | Met | Leu | Leu 755 | Glu | Leu | Gln | Ile | Val 760 | |

| CCT | ATA | CTA | AAT | TTG | GCT | TCG | GTA | CGT | GTA | GGT | AAC | CAT | CAC | AAC | GGG | 2598 |
|---|---|---|---|---|---|---|---|---|---|---|---|---|---|---|---|---|
| Pro | Ile | Leu | Asn | Leu 765 | Ala | Ser | Val | Arg | Val 770 | Gly | Asn | His | His | Asn 775 | Gly | |

| CCC | CAC | TCG | TAT | TTC | AAT | ACA | ACG | TAT | CTA | TCG | GTG | GAA | GTG | CGC | GAC | 2646 |
|---|---|---|---|---|---|---|---|---|---|---|---|---|---|---|---|---|
| Pro | His | Ser | Tyr 780 | Phe | Asn | Thr | Thr | Tyr 785 | Leu | Ser | Val | Glu | Val 790 | Arg | Asp | |

| ACA | AGC | GGT | GGT | GTT | GTG | TTT | TCG | TAT | TCA | CGC | CTC | GGT | AAC | GAA | CCG | 2694 |

|  |  |  |  |  |  |  |  |  |  |  |  |  |  |  |  |
|---|---|---|---|---|---|---|---|---|---|---|---|---|---|---|---|
| Thr | Ser | Gly 795 | Gly | Val | Val | Phe | Ser 800 | Tyr | Ser | Arg | Leu | Gly 805 | Asn | Glu | Pro |

```
ATG ACA CAC GAA CAT CAC AAA TTC GAA GTG TTC AAA GAT TAT ACA ATA        2742
Met Thr His Glu His His Lys Phe Glu Val Phe Lys Asp Tyr Thr Ile
    810             815             820

CAC TTG TTC ATA CAA GAA CCT GGC CAA AGG TTA CAA TTA ATA GTC AAC        2790
His Leu Phe Ile Gln Glu Pro Gly Gln Arg Leu Gln Leu Ile Val Asn
825             830             835             840

AAA ACA CTC GAC ACG GCG CTG CCC AAC TCT CAA AAC ATT TAC GCT CGC        2838
Lys Thr Leu Asp Thr Ala Leu Pro Asn Ser Gln Asn Ile Tyr Ala Arg
            845             850             855

CTC ACG GCC ACG CAA TTA GTA GTG GGA GAA CAG AGC ATT ATC ATT AGC        2886
Leu Thr Ala Thr Gln Leu Val Val Gly Glu Gln Ser Ile Ile Ile Ser
        860             865             870

GAC GAT AAC GAC TTT GTA CCG CCA CCA CCA CGC GTT AAT TGT GGC GAC        2934
Asp Asp Asn Asp Phe Val Pro Pro Pro Pro Arg Val Asn Cys Gly Asp
    875             880             885

CAG CAG ATA AGA GTA GTG GAA ACT TTA AAA ATG ATA GCG TTC                2976
Gln Gln Ile Arg Val Val Glu Thr Leu Lys Met Ile Ala Phe
890             895             900

TAGAAATTTT TTAACAAAAC ACAAAGTGAA TTGCAGTCGC TTGTTATCTT TGGCCACGGT      3036
ATGGCGCGCG CTTCGTATTA TGTGCTACTA CTATCCTTGG TGGTGTTATC GGTTAATGGA      3096
TATTCGTTTT ATTCGTCCAT CGAAGCCCTA CTTTGAACG ATCGCACACA AATCTGCATT       3156
GGCGATTGTT ACGAGCGCAA CGGTCAACAT                                       3186
```

( 2 ) INFORMATION FOR SEQ ID NO:2:

( i ) SEQUENCE CHARACTERISTICS:
        ( A ) LENGTH: 902 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Tyr Asn Val Ile Val Pro Thr Thr Val Leu Pro Pro Trp Leu
1               5                   10                  15

Arg Ile Gly Gln Asn Trp Ile Phe Ala Arg His Arg Arg Thr Glu Val
            20                  25                  30

Gly Val Val Leu Pro Ala Asn Thr Lys Phe Arg Val Arg Ala Asp Phe
        35                  40                  45

Ala Lys Trp Gly Ile Thr Arg Pro Val Ile Val Arg Leu Leu Asn Asn
    50                  55                  60

Asn Arg Asn Thr Glu Arg Glu Ile Asn Leu Thr Asn Asp Gln Trp Ile
65                  70                  75                  80

Glu Met Glu His Glu His Glu Cys Val Pro Phe Val Asp Trp Pro Val
                85                  90                  95

Gly Glu Lys Asn Thr Met Ala Glu Val His Phe Glu Ile Asp Gly Pro
            100                 105                 110

His Ile Pro Leu Pro Val Tyr Val Phe Asn Thr Arg Pro Val Glu Asn
        115                 120                 125

Phe Lys Ser Glu Tyr Arg Gln Ser Ser Ser Gly Tyr Cys Phe Leu Tyr
    130                 135                 140

Leu Asp Leu Val Cys Ile Leu Val Pro Pro Ala Ser Lys Asn Val Leu
145                 150                 155                 160

Leu Asp Thr Asp Leu Phe Glu Leu His Gln Phe Tyr Asn Glu Ile Ile
                165                 170                 175
```

```
Asn Tyr Tyr Asp Asp Leu Cys Gly Leu Val Glu Asp Pro Tyr Ala Asp
            180                 185                 190

Thr Val Asp Ser Asn Leu Pro Asn Lys Ala Ala Phe Val Lys Ala Asp
        195                 200                 205

Gly Gly Gly Pro Gly Gly Ala Tyr Gly Ala Phe Trp Thr Ala Pro
    210                 215                 220

Ala Ser Thr Asn Leu Gly Glu Tyr Leu Arg Val Ser Pro Thr Asn Trp
225                 230                 235                 240

Met Val Ile His Glu Leu Gly His Ala Tyr Asp Phe Val Phe Thr Val
                245                 250                 255

Asn Thr Arg Leu Ile Glu Ile Trp Asn Asn Ser Phe Cys Asp Arg Ile
            260                 265                 270

Gln Tyr Thr Trp Met Asn Lys Thr Lys Arg Gln Gln Leu Ala Arg Ile
        275                 280                 285

Tyr Glu Asn Gln Arg Pro Gln Lys Glu Ala Ala Ile Gln Ala Leu Ile
    290                 295                 300

Asp Asn Asn Val Pro Phe Asp Asn Trp Asp Phe Phe Glu Lys Leu Ser
305                 310                 315                 320

Ile Phe Ala Trp Leu Tyr Asn Pro Gln Arg Gly Leu Asp Thr Leu Arg
                325                 330                 335

Asn Ile Asn His Ser Tyr Arg Leu His Ala Ala Arg Asn Pro Val Thr
            340                 345                 350

Pro Tyr Pro Gln Ile Trp Ala Trp Leu Met Ser Cys Gly Tyr Asp Asn
        355                 360                 365

Phe Trp Leu Tyr Phe Asn Arg Ile Gly Leu Tyr Pro Ala Asp Phe Tyr
    370                 375                 380

Ile Asn Glu His Asn Lys Val Val His Phe Asn Leu His Met Arg Ala
385                 390                 395                 400

Leu Ala Leu Gly Gln Ser Val Arg Tyr Pro Ile Lys Tyr Ile Ile Thr
                405                 410                 415

Asp Phe Asp Leu Leu Gln Lys Asn Tyr Asp Ile Lys Gln Tyr Leu Glu
            420                 425                 430

Ser Asn Phe Asp Leu Val Ile Pro Glu Glu Leu Arg Gln Thr Asp Leu
        435                 440                 445

Val Ala Asp Val Arg Val Val Cys Val Ile Asp Asp Pro Ser Gln Ile
    450                 455                 460

Ile Gly Glu Pro Phe Ser Leu Tyr Asp Gly Asn Glu Arg Val Phe Glu
465                 470                 475                 480

Ser Thr Val Ala Thr Asp Gly Asn Met Tyr Leu Val Gly Val Gly Pro
                485                 490                 495

Gly Val Tyr Thr Leu Arg Ala Pro Arg Gly Lys Asp Lys Arg Tyr Lys
            500                 505                 510

Leu His Leu Ala His Ser Pro Asn Glu Pro Val His Pro Ala Asn Asp
        515                 520                 525

His Met Tyr Leu Leu Val Thr Tyr Pro Tyr Tyr Asn Gln Thr Leu Thr
    530                 535                 540

Tyr Thr Arg Tyr Ile Thr Ser Asp Leu Ala Ile Asp Ala Ala His Leu
545                 550                 555                 560

Phe Gly Thr Asp Arg Leu Tyr Val Ala Thr Ile Tyr Phe Asp Ala Leu
                565                 570                 575

Gln Gln Thr Val Thr Val Tyr Leu Asn Asn Ile Arg Thr Gly Arg Glu
            580                 585                 590

Asn Asn Thr Thr Leu Tyr Phe Glu Met Glu Ile His Asn Pro Phe Ile
        595                 600                 605
```

```
Gly Thr Ser Ser Lys Phe Thr Leu Leu Glu Asp Asn Val Thr Met Arg
    610             615                 620
Gln Gly Tyr Tyr Lys Phe Pro Ala Val Thr Phe Ser Ser Ile Arg Leu
625                 630                 635                     640
His Ile Arg Asp Asp Asn Arg Leu Met Leu Val Asp Lys Tyr Leu Pro
            645                 650                     655
Ala Gly Asp Thr Leu Leu Phe Met Phe Pro Asn Gln Ile Val Asp Asn
            660                 665                     670
Asn Ile Phe Pro Asp Gly Ser Ile Leu Thr Ser Thr Tyr Asn Arg Ile
        675                 680                 685
Lys Glu Gln Ala Ala Phe Ile Glu Asn His Lys Gln Leu Leu Tyr Ile
    690                 695                 700
Glu Asn Glu Leu Arg Asp Ser Ile Tyr Leu Ala Ser Gln Phe Val Asn
705                 710                 715                     720
Ser Asp Ser Asn Glu Phe Leu Lys Tyr Phe Pro Asp Tyr Phe Arg Asp
                725                 730                 735
Pro His Thr Phe Ser Tyr Leu Phe Arg Phe Arg Gly Leu Gly Asp Phe
            740                 745                 750
Met Leu Leu Glu Leu Gln Ile Val Pro Ile Leu Asn Leu Ala Ser Val
        755                 760                 765
Arg Val Gly Asn His His Asn Gly Pro His Ser Tyr Phe Asn Thr Thr
    770                 775                 780
Tyr Leu Ser Val Glu Val Arg Asp Thr Ser Gly Gly Val Val Phe Ser
785                 790                 795                     800
Tyr Ser Arg Leu Gly Asn Glu Pro Met Thr His Glu His His Lys Phe
            805                 810                 815
Glu Val Phe Lys Asp Tyr Thr Ile His Leu Phe Ile Gln Glu Pro Gly
        820                 825                 830
Gln Arg Leu Gln Leu Ile Val Asn Lys Thr Leu Asp Thr Ala Leu Pro
        835                 840                 845
Asn Ser Gln Asn Ile Tyr Ala Arg Leu Thr Ala Thr Gln Leu Val Val
    850                 855                 860
Gly Glu Gln Ser Ile Ile Ile Ser Asp Asp Asn Asp Phe Val Pro Pro
865                 870                 875                     880
Pro Pro Arg Val Asn Cys Gly Asp Gln Gln Ile Arg Val Val Glu Thr
            885                 890                 895
Leu Lys Met Ile Ala Phe
            900
```

DNA SEQUENCE CODING FOR ENHANCIN POLYPEPTIDE WHICH ENHANCES VIRUS INFECTION OF HOST INSECTS

REFERENCE TO RELATED APPLICATIONS

This is a continuation-in-part patent application of a copending parent provisional patent application Ser. No. 60/002,743, filed Aug. 24, 1995 now abandoned.

FIELD OF THE INVENTION

The invention relates to the cloning and sequencing of novel viral genes from certain baculoviruses for insect control. More particularly, the invention relates to an isolated and cloned DNA from a virus which encodes an amino acid sequence of a polypeptide isolated from occlusion bodies of certain baculoviruses and which enhance baculovirus infectivity, termed herein as "enhancins".

BACKGROUND OF THE INVENTION

The Baculoviridae, comprised of the nucleopolyhedroviruses (NPV) and granuloviruses (GV), are a family of viruses that primarily infect insects. Autographa californica multiple NPV (AcMNPV) is the best studied insect virus. Well developed in vitro systems have permitted extensive molecular characterization. In addition, it is utilized as a tool for foreign gene expression and an alternative to chemical pesticides In 1959 a protein, the synergistic factor (SF), was identified that increased the susceptibility of *Pseudaletia unipuncta* larvae to a dual infection by both PsunGV-H and a PsunNPV (Tanada, 1959). The SF was estimated to be present at levels up to 5% of the granulin protein (Tanaria, 1985). The granules of the cabbage looper granulovirus, *Trichoplusia ni*, TnGV, also contain a protein, the enhancin (Derksen & Granados, 1988; Corsaro et al., 1993) that enhances infections of AcMNPV and other viral species like the *T. ni* single enveloped nucleopolyhedrovirus TnSNPV (Greenspan Gallo et al., 1991).

The exact mechanisms of enhancement are unknown, but two different modes of action have been proposed. The PsunGV-H enhancin was reported to interact with viral particles and increase the binding of the latter to the insect midgut microvilli (Tanada, 1985). Studies on the mode of action of the VEF isolated from *Trichoplusia ni* (cabbage looper) granulovirus virus (TnGV) showed that the VEF caused rapid degradation of the peritrophic membrane which lines the midgut lumen of lepidopteran larvae. Larval bioassays suggested that this alteration made the peritrophic membrane more permeable to invading baculoviruses resulting in at least a 25-fold increase in larval mortality.

Closely related to, or identical with, the VEF protein is a lipoprotein, originally isolated in crude form from a Hawaiian strain of *Pseudaletia unipuncta* granulovirus virus (PuGV-H), but not cloned or sequenced. It is described by Tanaria and co-workers as the "synergistic factor" (SF) and as having a calculated molecular weight between 90 K and 160 K. The SF was released from the capsule upon dissolution in the midgut, and was the localized to the microvillar surface of the midgut cell membrane where it caused an apparent increase in the uptake of enveloped nucleocapsids. The binding of SF to the midgut membrane was found to be specific with a calculated equilibrium constant of $1.57 \times 10^{-9}$ M.

It was postulated that the two proteins (VEF and SF) are closely related and have similar dual modes-of-action: peritrophic membrane disruption and increased virus uptake. Evidence to support this relationship comes from southern hybridization's of PuGV-H genomic DNA with the VEF gene and western blots of dissolved PuGV-H occlusion bodies with an anti-VEF polyclonal antiserum. Tanada determined that this SF in the capsule of PuGV-H increased the larval susceptibility to *P. unipuncta* nuclear polyhedrosis virus (PuNPV). This was confirmed by the sequence similarity shown in U.S. Pat. No. 5,475,050.

These proteins are referred to herein generally as "enhancins", but are also referred to as virus enhancing factors (VEF) and/or as synergistic factors (SF). Genes encoding enhancins (VEF and SF) and pest control compositions comprising this factor and nuclear polyhedrosis viruses are the subject matter of U.S. Pat. Nos. 5,475,090, 4,973,667, and 5,011,685. Since viral enhancing proteins are important at early stages of host infection, it is important to identify and locate the genes for other similar proteins within the viral genome. A need, therefore, exists to clone and sequence the genes of other related proteins. It is an object of this invention to satisfy such a need.

SUMMARY OF THE INVENTION

The invention relates to the cloning and sequencing of novel viral genes from certain baculoviruses for insect control. More particularly, the invention relates to an isolated and cloned DNA from a granulovirus virus which comprises an amino acid sequence of the viral gene encoding a polypeptide isolated from occlusion bodies of certain baculoviruses and which polypeptide possesses the biological activity of enhancing baculovirus infectivity. This invention also relates to isolated and purified baculovirus proteins which are characterized by enhancing the infectivity of baculoviruses. Such proteins termed herein as "enhancins" are found within the viral occlusion body, have a disruptive effect on the insect peritrophic membrane (PM) proteins, and/or interact with the midgut epithelium in such a manner as to permit the increased adsorption, penetration and uptake of virus particles by midgut cells with a concomitant increase in host mortality. The invention relates to the cloning and sequencing of a novel viral gene.

The present invention includes a recombinant DNA sequence which codes for the enhancin protein of the *Helicoverpa armigera* granulovirus virus. The DNA sequence is shown in SEQ. ID. NO.: 1 and the open reading frame is shown in SEQ. ID. NO.: 1: base pairs 271–2976. The amino acid sequence of the enhancin protein is shown in SEQ. ID. NO.: 2: base pairs 1–901, which has two domains one stretching from residues 1–550, and the other from 551–901.

A recombinant protein can be produced from this newly isolated DNA sequence with an expression vector comprising the DNA sequence and a suitable promoter which, when put into a suitable host will be capable of resulting in the expression of an amino acid sequence having the physical, chemical, and/or biological properties of the enhancin protein of the *Helicoverpa armigera* granulovirus virus. The expression vector can be either a recombinant plasmid adapted for transformation of a microbial host or recombinant baculovirus.

A recombinant plasmid which includes a recombinant DNA sequence which codes for the enhancin protein of the *Helicoverpa armigera* granulovirus virus was used to transform *E. coli* and deposited at the Agricultural Research Service Culture Collection (NRRL), Northern Regional Research Center, Agricultural Research Service, U.S.

Department of Agriculture, 1815 North University Street, Peoria, Ill. 61604 and assigned accession number: NRRL B-21614.

The recombinant enhancin protein, and/or the recombinant baculovirus for expressing the enhancin protein can be used in a composition toxic to insects along with a compound toxic to insects. The activity of the composition is partially through the action of the enhancin, the enhancin having a disruptive effect on the insect peritrophic membrane proteins such that it interacts with the midgut epithelium in such a manner as to enhance the increased absorption, penetration, and/or uptake of virus by midgut cells with a corresponding increase in host mortality.

A more complete appreciation of the invention and the advantages thereof will be apparent as the same becomes better understood by reference to the following details of description when considered in connection with the accompanying drawings.

BRIEF DESCRIPTION OF THE DRAWING

FIGS. 1a and 1b show a comparison of the amino acid sequences of the *Pseudaletia unipuncta, Trichoplusia ni* and *Helicoverpa armigera* enhancins.

DESCRIPTION OF THE PREFERRED EMBODIMENT

One of the discoveries of the present invention is the cloning and sequencing of the enhancin gene found in the *Helicoverpa (Heliothis) armigera* granulovirus (HearGV). While, the enhancin gene found in the PsunGV-H virus is virtually identical to the previously characterized *Trichoplusia ni* GV (TnGV) enhancin gene, a comparison of the predicted amino-acid (aa) sequences of TnGV enhancin (901 aa) with the HearGV enhancin (902 aa) revealed herein demonstrated an overall identity of only 80%, with greater conservation (88%), and hence higher homology, from amino-acids 1–550. The addition of the newly discovered HearGV enhancin to an AcMNPV inoculom increased the infectivity of baculoviruses in insect larvae. This discovery will aid in the effort to control certain pests without the use of pesticides.

Moreover, the host range of the *Helicoverpa (Heliothis) armigera* granulovirus is significantly broader than that of other known granulovirus viruses, such as TnGV or PuGV, which suggests that the HearGV enhancin disclosed herein may have broader biological activity, increasing its potential effectiveness in the control of insects (John J. Harem, 1982, incorporated herein by reference). A pathogen, here a insect baculovirus, that is an effective microbial control against several species of economically damaging insects, as is HearGV due to its broad specificity, is much more useful against a complex of insects attacking a crop and therefore more economically viable as a commercially useful insect pathogen than a similar enhancin with a narrower insect target range.

I. Identification of Enhancins in Granulovirus Species

Proteins from eight different granuloviruses that infected 4 different Lepidopteran families were analyzed by SDS-PAGE and Western blotting in an attempt to identify novel enhancin proteins. The granulovirus (GV) species used in this study were: CpGV, *Estigmene acrea* (EsacGV), *Heliocoverpa armigera* (HearGV), PlinGV, *Pieris rapae* (PiraGV), PsunGV-H, *Scotogramma trifiolii* (SctrGV) and TnGV. Viral stocks were maintained in the lab as granule suspensions and/or infectious hemolymph isolated from previously infected larvae. Larval infections, purification of granules and enhancin was as previously described (Derksen & Granados, 1988; Greenspan & Gallo et at., 1991, both incorporated herein by reference).

For the SDS-PAGE and Western blot analysis granules were dissolved in 100 mM NaHCO$_3$ (pH 10.5) and incubated at room temperature for 15 minutes. The protein concentration was determined using the Bradford assay kit (Promega Corp., Madison, WI). Approximately 10 µg of each GV solution was analyzed on SDS-PAGE. Gels were silver stained. A duplicate gel was transferred onto PVDF membrane (NEN Research Products, Dupont, Boston, MA) using a protocol provided by the manufacturer (Biorad, Melville, NY). Western blots were analyzed using a rabbit anti-VEF-TrpE polyclonal antibody at a dilution of 1:5000. Cross-reactive bands were visualized using goat anti-rabbit alkaline phosphatase conjugated secondary antibody, this was done at a dilution of 1:3000 (Sigma, St. Louis, MO).

Five different GV species, four infecting the *Noctuidae* family and one infecting the *Pieridae* family, were found to contain proteins that did cross-react with the anti-enhancin polyclonal antibodies already mentioned. However, PlinGV, which infects indian meal moth larvae (*Noctuidae*), CpGV, that infects codling moth larvae (*Torticidae*) and EsacGV, that infects saltmarsh caterpillar larvae (*Arctiidae*), were not seen to have crossreacting proteins. Two granulovirus species, *C. pomonella* GV, and *E. acrea* GV, were previously identified as having an enhancin, and were used as positive controls in the research herein disclosed. We also used standard neonate bioassays performed with both EaGV and CpGV, in attempt to demonstrate enhancin activity therein, however, neither displayed any ability to enhance the infectivity of baculovirus.

The enhancins can be subdivided into of three different groups based on their respective molecular weights, and migration patterns: 104 kD for the TnGV, PsunGV-H and PiraGV enhancins, 108–110 kD for HearGV enhancin and 120 kD for SctrGV enhancin. In standard *T. ni* neonate bioassays HearGV, PsunGV-H and SctrGV demonstrated an ability to "enhance" the level AcMNPV infectivity, confirming the presence of an enhancin. PsunGV-H, was the first granulovirus for which the presence of an enhancin in its occlusion body was described and documented.

A. Cloning and Sequencing

Vital genomic DNA was isolated from granules as described by Smith and Summers (1982), incorporated herein by reference. All of the restriction endonucleases and modifying enzymes were purchased from Promega Corp. (Madison, WI). Restriction endonucleases were routinely used in DNA digests using a universal enzyme restriction endonuclease buffer (10x=0.33 M Tris/Acetate pH 7.85, 0.65 M Potassium acetate, 0.1 M Magnesium acetate, 0.04 M Spermidine Tri-Chloride, 5 mM Dithiothreitol). DNA gel electrophoresis, Southern blotting and hybridization were performed as described (Hashimoto et al., 1991). Viral genomic DNA was cloned into either plJC18/19 (YanischPerron et at., 1985) or Bluescript SK (Stratagene, La Jolla, CA).

The complete HearGV enhancin gene was identified through hybridization of a 1.75 Kb KpnI fragment of the HearGV gene, that crosshybridized to a TnGV internal enhancin fragment on a blot, where the HearGV genomic DNA had been digested with BamHI, EcoRI, HindIII and KpnI. A cross-hybridizing BamHI fragment with an estimated size of 5.2 Kb was cloned into the pUC18 expression vector and a DNA restriction map was thereafter generated. The KpnI fragment already mentioned, as well as the 1.45 Kb SstII-BamHI fragment, and deletion fragments derived thereof, were sequenced on both strands.

HearGV genomic clones were sequenced using cesium chloride purified DNA and a commercially available sequencing kit (United States Biochemical Corp., Cleveland, OH). Deletion clones were generated by Bal31 digestion as described, the Erase-a-Base ExoIII/S1 digestion kit (Promega Corp., Madison, WI) or an ExoIII/Mung bean nuclease kit (Stratagene). Sequence products were analyzed on gels prepared with 6% Sequagel Rapid Sequencing Solution (National Diagnostics, Atlanta, GA). Sequence information from the generated genomic clones was developed through the use of the Sequence Analysis Software Package of the Genetics Computer Group (Madison, WI, Versions 7.2 and 7.3).

The enhancin gene from HearGV was cloned and sequenced as described above. Every nucleotide on both strands of the enhancin gene sequence was sequenced a minimum of 2 times. The DNA sequence and deduced amino acid sequence of the HearGV gene is shown in SEQ. ID. NO: 1 and SEQ. ID. NO: 2, respectively. Sequence data analysis of the HearGV DNA revealed an open reading frame (ORF) of 2706 nucleotides that encodes a protein containing 902 amino acids and a mass of 104.6 kD. Similarly, PsunGV-H clones have an ORF of 2703 bp that encodes a protein of 901 amino acids with a mass of 104.2 kD. (Please note that the DNA and amino acid sequence for PsunGV-H and TnGV enhancins are presented in the Sequence Listing of U.S. Pat. No. 5,475,090).

B. Isolation of RNA and Primer Extension Analysis

Total RNA was isolated from HearGV infected *T. ni* larvae at daily intervals from 0–8 days post infection (p.i.), using guanidine isothiocyanate (GIT) as described (Sambrook et at., 1989 inc. by ref.). Four to eight larvae were collected for each timepoint, frozen in liquid nitrogen and then ground in a glass Potter tube in the presence of 4 ml of GIT. The resulting larval suspension was layered onto a CsCI gradient and spun for 16 hours at 35 K. The RNA pellet was then collected, precipitated, washed, dried and quantified.

For primer extension analysis of the enhancin promoter, a primer (HAZR2) 5' CAC GGC GGC AGC ACG G 3' complementary to nucleotides 43-28 downstream of the AUG initiator codon of the enhancin gene was used. Approximately 100 ng of the primer was labeled using 100 mCi of g-ATP (Dupont Company, Boston, MA) and T4 polynucleotide kinase (Promega Corp., Madison. WI). Five nanograms of the primer were incubated with 50 μg of total RNA isolated from HearGV infected *T. ni* larvae isolated at 1, 4, 5, 6, 7 and 8 days post infection. The primer extension reaction was according to Ausubel et at., (1989 inc. by ref.) with two modifications: the AMV reverse transcriptase (RVT) (Promega, Madison, WI) was incubated at 50° C. and actinomycin D was added at a final concentration of 75 μg/ml to inhibit the DNA-dependent DNA polymerase activity of the RVT. Reaction products were analyzed on a 6% polyacrylamide (PAA)-gel and compared to a sequencing ladder of clone HABAM, that contains a 5.2 Kb BamHI fragment from the HearGV genome and has the complete enhancin coding sequence also sequenced with the same primer.

C. Generating the Plasmid

For the analysis of the 5' end of the HearGV enhancin message, a 800 bp NcoI fragment from clone HABAM was subcloned in vector pSL1180 (Pharmacia, Piscataway, NJ) to yield pHANCO. A 470 bp MunI-BamHI fragment (425 bp HearGV sequences and 45 bp pSL1180 multilinker) was subcloned into Bluescript KS+digested with EcoRI and BamHI to yield pHAMB. To generate a probe complementary to the 5' end of the HearGV enhanein gene, plasmid pHAMB was linearized at the HindIII multilinker site, which lies upstream of the MunI/EcoRI fusion site. Transcription with T7-RNA polymerase (Gibco BRL, Gaithersburg, MD) was according to the manufacturer's protocol in the presence of 20 μCi UTP. After transcription, the template was digested for 15 minutes at 37° C. by adding 2 μl RNase free DNase (10,000 U/ml; Boehringer Mannheim, Indianapolis, IN). Following digestion, 100 μl TSE (TE plus 0.5% SDS) was added, followed by extraction with PCI (phenol/chloroform/isoamyl alcohol, 25:24:1). The probe was further purified by elution from a Nick G-50 gravity flow column (Pharmacia, Piscataway, NJ). Two microliters of the resulting purified probe were analyzed on a 6% polyacrylamide-gel. The presence of several premature stops further necessitated purification on a 6% PAA gel. The full length probe (530 nucleotides) was isolated from this gel.

For analysis of the 3' end of the enhancin message, clone HASB, which has a 1.45 Kbp SstII-BamHI fragment of the HearGV enhancin gene cloned into Bluescript SK-, was cut with MluI. An antisense T7 RNA probe was synthesized and purified as described above. Upon gel analysis the probe was found to be >95% full length (372 nucleotides) and used without further purification.

The HearGV gene inserted into the plasmid vector was transfected into *E. coli* and deposited under the Budapest Treaty on Aug. 22, 1996 at the Agricultural Research Service Culture Collection (NRRL), Northern Regional Research Center, Agricultural Research Service, U.S. Department of Agriculture, 1815 North University Street, Peoria, Ill. 61604 and assigned accession number: NRRL B-21614. The applicant agrees to be bound by the terms of the Budapest Treaty regarding availability.

D. RNAse Protection Analysis

For RNase protection analysis, 20 μg of total RNA were mixed with 105 cpm of antisense RNA probe, precipitated and resuspended in 30 μl of hybridization buffer (80% formamide, 40 mM PIPES, 400 mM NaCl, 1 mM EDTA). After heating for 10 minutes at 80° C., the mixture was left to hybridize overnight at 50° C. Following hybridization, unprotected RNA was digested by adding 350 μl RNase mix (10 mM Tris pH 7.5, 5 mM EDTA, 0.3 M NaCl, 2 μl 10 mg/ml RNase A, 5 μl 100,000 U/ml RNase T1) and incubated at 30° C. for 60 minutes. The digestion was stopped by adding SDS to a final concentration of 0.5%. Samples were further purified by digestion with Proteinase K (3 μl of a 15 mg/ml premix; Boehringer Mannheim) for 30 minutes at 37° C. The samples were extracted twice with 400 μl PCI and precipitated at room temperature (RT) for 30 minutes by addition of 1 ml of 96% ethanol. Samples were spun at room temperature, washed twice with 70% ethanol at room temperature, dried briefly and resuspended in 20 μl loading buffer (50% formamide, BFB and XCFF 0.05%).

Reaction products were analyzed on 6% polyacrylamide sequencing (3' analysis) or slab gels (5' analysis). Product sizes were estimated by comparison to a sequencing ladder of clone HABAM sequenced with primer HAZR2 and comparison to a 123 bp ladder (GIBCO BRL). Gels were exposed to XAR 5 film in cassettes with intensifying screens (Kodak, Rochester, NY).

The RNase protection analysis of the 3'end of the HearGV enhancin offers some evidence both for transcription termination and transcriptional read through into the second ORF. No canonical polyadenylation signal AAUAAA, was present upstream of the transcription termination signal. An alternative poly(A) sequence closely resembling the poly(A) sequence, AACAAA, was present between nucleotides 3003–3008. It has been reported that the presence of a similar sequence downstream of the β-thalassaemia gene or other alternative poly(A) like sequences results in elongated and unstable transcripts and changes to the steady state levels of mRNA. This may explain why, apart from the two major protected RNA species during RNase protection, several minor protected species appeared to be protected. Alternatively, it is possible that the HearGV enhancin gene transcript does not have a poly(A) tail. This would not be unique for baculoviruses. Recently, a convincing case has been made for the absence of a poly(A) tail on *Spodoptera exigua* NPV polyhedrin mRNA.

The 3' RNase protection assay also indicated that the enhancin ORF and the downstream ORF maybe on one message. The occurrence of bi-cistronic messengers is not uncommon for baculoviruses. Analysis of the HindIII-M region of *Orgyia pseudotsugata* NPV for instance, has shown that hi,- and multi-cistronic messages originated from baculovirus late promoter motifs that had different 5' ends but the same 3' end.

E. Transcriptional Analysis of the Enhancin Genes

Transcriptional analysis of the HearGV gene reveals several more interesting features of enhancin genes. Of the three baculovirus late promoter motifs conforming to the consensus NTAAG sequence, present in the region upstream of the enhancin ORF the one that is predominantly used, TTAAG, is positioned only 3 nucleotides from the translational AUG start codon. Transcriptional analysis of the TnGV enhancin gene has also shown that the ATAAG motif present at −8 to −4 relative to the AUG initiator codon serves as the only transcriptional initiation point.

From our work it has become clear that the AUG closest to the promoter is the translation initiation codon. That this codon is the translation initiator codon is based on several observations seen infra. First, the context of the initiator codon −3 AUCAUGC+4 is similar to the Kozak consensus sequence for translation initiation, −3 A/GYYAUGG+4. The pyrimidine C present at position +4 in the HearGV gene, and in all enhancin genes sequenced so far, is the only notable exception to the Kozak consensus. It has been found through mutation studies that replacement of the consensus G in position +4 acts to downregulate eukaryotic translation. Second, the mass of the protein observed in protein gels corresponds well with the first AUG in the ORF acting as the translational initiator codon. Third, the next possible AUG lies 240 nucleotides downstream in the coding region and does not confer to Kozak rules at all.

The observation that a baculovirus late promoter in the HearGV gene is present so proximal to the start codon that upon transcription it gives rise to a 5' leader with a maximum length of 7 nucleotides, is unique to the enhancin genes, and has only been previously reported for the TnGV enhancin gene. Leaders of eukaryotic messages are seldom shorter than 7–10 nucleotides and usually average between 25 and 50 nucleotides. Deletion studies of the 5' non-coding region on the translational efficiency of phosphoglycerate kinase mRNA in yeast, for instance, have shown that even if the leader length is decreased to 7 nucleotides, translation at 50% of the optimal rate still occurs. The observation that a shorter leader impairs the fidelity of initiation by eukaryotic ribosomes, has been confirmed using an in vitro transcription and translation system (Kozak, 1991, inc. by ref.). This negative effect on fidelity of initiation, however, can be almost completely eliminated by the presence, or through the introduction of, secondary structure with a DG of −19 kcal/mol in the mRNA at an optimal distance of 14 nucleotides from the AUG initiator codon (see, Kozak, 1990, 1991).

Transcription of the HearGV enhancin gene also results in a short 5' leader sequence with considerable secondary structure (DG −16.7 kcal/mol: GCG MFold analysis) within the first 100 nucleotides of the mRNA. The total amount of enhancin present in granules has been estimated to be 5% of total protein. This suggests that enhanein gene promoters are rather strong. The combination of promoter proximity, suboptimal AUG context and secondary structure downstream of the AUG initiator codon, may very well result in a complex mechanism of transcription regulation, mRNA stability, and translation efficiency unique to baculoviruses II. Comparisons of Homology After sequencing the HearGV enhancin gene, as laid out above, it was determined that it shared significant sequence homology with both the TnGV and PsunGV-H enhancin genes (see Table 1 below). Analysis of this similarity in sequence between the PsunGV-H and HearGV enhancin genes at the DNA and deduced amino acid sequence level, and thereafter comparison with the TnGV enhancin gene sequence revealed several interesting characteristics of the genes, and their respective homology. The TnGV and PsunGV-H enhancin genes are virtually identical from 325 nucleotides upstream of the enhancin ORF and throughout the partial ORF identified downstream of the enhancin gene. Since in HindIII digests of TnGV and PsunGV-H genomic DNA, 19 of the 26 visible fragments comigrate the observed conservation of homology suggests that both granuloviruses are strongly related and may have only recently evolved divergently.

TABLE 1

Comparison of the TnGV, PsunGV-H and HearGV DNA and amino acid sequences

| | Nucleotide Sequence Identity | | | | | |
|---|---|---|---|---|---|---|
| Virus Compare | Upstream 450-325 n | Upstream 334-65 n | Upstream 65-1 n | Overall ATG-Stop | Intergenic Region | Downstream ORF |
| Ha × Tn | ND | ND | 40% | 77% | 46% | 73% |
| Ha × Pu | ND | 38% | 40% | 77% | 46% | 69% |
| Pu × Tn | 35% | 94% | 100% | 99% | 100% | 98% |

| | Amino Acid Sequence Identity | | | | | | | | | |
|---|---|---|---|---|---|---|---|---|---|---|
| | Overall 1-end | | Amino Acid 1-551 | | Amino Acid 551-end | | Downstream ORF | | Downstream ORF 20-end | |
| Virus Compare | ID | SIM | ID | SIM | ID | SIM | ID | SIM | ID | SIM |
| Ha × Tn | 80% | 90% | 88% | 94% | 68% | 83% | 82% | 89% | 93% | 98% |
| Ha × Pu | 81% | 90% | 89% | 95% | 69% | 84% | 78% | 86% | 95% | 100% |
| Pu × Tn | 98% | 99% | 99% | 99% | 97% | 99% | 94% | 97% | 100% | 100% |

ND: Not Determined ID: Identity SIM: Similarity n: nucleotide

A comparison of the PsunGV-H and TnGV enhancin genes (FIG. 1 & Table 1), showed that they are virtually identical at both the DNA and the amino acid sequence level over almost their entire length. The amino acid sequences differ in only fifteen amino acids. Seven changes are caused by a 21 nucleotide reciprocal frameshift (reflected by the dissimilarity in amino acids 652–658, FIG. 4). The remaining eight amino acid changes are caused by point mutations in the PsunGV-H enhancin gene. The DNA homology from –450 through –325 nucleotides upstream of the translational initiator codon is 35%. This increases to 94% from –325 to –1 and 98% for the remaining DNA. There is a 98 % identity for the peptide sequences.

When the HearGV and PsunGV-H enhancin genes are compared, virtual identity is not present (FIG. 1 & Table 1). For 270 nucleotides upstream of the translational start codon the homology is 40%. This increases to an overall homology of 77% within the ORF, decreases to 46% for the intergenic region and increases again to 69% for the putative downstream ORF. Comparison of the amino acid sequences of the two enhancins revealed that the overall identity and similarity are 81% and 90% respectively. Amino acids 1–550 show an identity and similarity of 89% and 95%. This similarity decreases to 69% and 84%, when amino acids 551–902, respectively, are compared. While amino acid sequences 1–550 score significantly above the similarity average, the amino acids 551–901 scored significantly below it, when the GCG PlotSim software program is used to generate a similarity comparison.

A. Genetic Analysis

The above analysis demonstrates that enhancins have two distinct domains. This may be a reflection of the fact that two activities have been found to be associated with enhancins, namely the breakdown of peritrophic membranes through a proteolytic activity and the enhancement of viral binding to receptors present in the midgut microvilli.

The HearGV gene has a consensus baculovirus late promoter motif shared with the PsunGV-H gene (PsunGV-H: ATAAG; HearGV: TTAAG,) at positions –8 through –4 relative to the translational start codon. Two other late motifs, GTAAG and ATAAG, were present in the HearGV sequence within 270 basepairs upstream of the ATG. The PsunGV-H sequence has no other late promoter motifs within 400 nucleotides upstream of the AUG. A second late promoter motif, ATAAG was present at 36-32 nucleotides upstream of the enhancin translational stop codon (positions 2991–2993) with the start codon of a putative ORF (PsunGV-H: 3057–3059; HearGV: 3051–3053) downstream of it. No canonical polyadenylation consensus sequences were identifiable in the short intergenic region between the translational stop codon of the enhancin gene and the translational start codon of the downstream ORF. It was noted however, that the HearGV DNA sequence here is relatively AT rich, and the PsunGV-H enhancin gene has two sequential stop condons, TAATAA. Either of these DNA sequences may meet the requirements for polyadenylation sites.

B. Genetic Divergence HearGV Enhancin Gene Sequence

The HearGV enhancin gene has several baculovirus late promoters upstream of the enhancin ORF and encodes a significantly different protein from previously described enhancins, one which differs in both mass and deduced amino acid sequence from the enhancin of TnGV and PsunGV-H. Therefore it is a separate and novel gene product from previously described genes.

While the HearGV enhancin has 902 amino acids and a mass of 104.6 kD, it migrates at a higher than expected mass of 108–110 kD. We hypothesize that this variant migration behavior may be caused by the presence of a sequential stretch of proline residues at the C-terminal end of this sequence (positions 880–883), that is lacking from the PsunGV-H sequence.

Comparison of the partial amino acid sequence of the downstream ORF (HearGV: AUG=3051, PsunGV-H: AUG= 3057) shows an identity and similarity of 82 and 89%, respectively (FIG. 5; Table 1). Analysis of the amino acid sequences with a GCG program that recognizes signal sequences with a probability of 95% and an accuracy of 75% at a score level of 3.5, revealed that the first twenty amino acids of both the HearGV and the PsunGV-H downstream ORF, most likely encode a similar signal sequence (the signal cleave scores are 8.8 and 7.3 respectively). The PsunGV-H downstream ORF has been shown to be open for at least 170 amino acids.

The organization, transcription and translation of these enhancin genes hold several special features that can be modulated to serve as useful alternatives to the application of chemical pesticides for insect management. As Table 2, below, demonstrates that the use of enhancin proteins, specifically the HearGV enhancin protein, dramatically affects the mortality of host larvae (see Table 2 below). Also as seen in Table 2, the amounts of the enhancins needed to substantially increase insect host mortality are very small.

TABLE 2

The Use of Various Enhancin Proteins to Increase the Infectivity of Baculoviruses, and Thereby the Mortality in Treated Insect Larvae

| Enhancin Concentration | Percent Mortality | | | |
|---|---|---|---|---|
| | Tn | Ha | St | Pu |
| Trial 1   0.1 ng | 100% | 100% | 100% | 100% |
| 0.01 ng | 97% | 90% | 90% | 97% |
| Trial 2   0.1 ng | 90% | 100% | 97% | 100% |
| 0.01 ng | 97% | 90% | 90% | 100% |

Percent mortality in T. Ni neonate larvae following ingestion of one AcMNPV OB per larva at two different concentrations of enhancin derived from four different granulovirus viruses. AcMNPV control at 1 OB/larva was 50% and 47% for 2 replications; Tn= *Trichoplusia ni* GV; Ha = *Heliothis armigera* GV; St = *Scotogramma trifolii* GV; Pu = *Pseudaletia unipuncta* GV.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. An isolated DNA sequence selected from the group consisting of:
   a) a DNA sequence which codes for the amino acid sequence of SEQ ID NO. 2;
   b) a DNA sequence having the sequence of SEQ ID NO. 1;
   c) a DNA sequence which codes for the residue 1–550 amino acid sequence of SEQ ID NO. 2; and
   d) a DNA sequence which codes for the residue 551–901 of amino acid sequence of SEQ ID NO. 2.

2. A recombinant expression vector comprising the DNA sequence of claim 1 and a suitable promoter capable of expressing said sequences in a suitable host.

3. The recombinant protein encoded by the DNA of claim 1.

4. A recombinant DNA sequence which codes for the enhancin protein of the *Helicoverpa armigera* granulovirus.

5. The recombinant protein encoded by the DNA sequence of claim 4, where the protein has a disruptive effect on the insect peritrophic membrane proteins such that it interacts with the mid gut epithelium in a manner to enhance absorption, penetration, and/or uptake of virus by midgut cells with a corresponding increase in host mortality.

6. A recombinant plasmid adapted for transformation of a microbial host, said plasmid comprising a plasmid vector into which a DNA segment which codes for the *Helicoverpa armigera* granulovirus virus enhancin protein.

7. The plasmid of claim 6, wherein said plasmid has all of the identifying characteristics of the plasmid deposited at the Agricultural Research Service Culture Collection (NRRL), Northern Regional Research Center, Agricultural Research Service, U.S. Department of Agriculture, 1815 North University Street, Peoria, Illinois 61604 and assigned accession number: NRRL B-21614.

8. The recombinant protein encoded by the plasmid of claim 6.

9. A composition toxic to insects comprising an enhancin encoded by the DNA sequence of claim 1 and a second material toxic to insects, wherein the activity of such composition is partially through the action of said enhancin, said enhancin having a disruptive effect on the insect peritrophic membrane proteins such that it interacts with the midgut epithelium in such a manner as to enhance the absorption, penetration, and/or uptake of virus by midgut cells with a corresponding increase in host mortality.

10. The expression vector of claim 2 wherein the vector is a recombinant baculovirus.

11. The baculovirus of claim 10 further comprising DNA coding for a compound toxic to insects, the activity of such composition is partially through the action of said baculovirus when ingested by insects.

12. The expression vector recombinant baculovirus vector of claim 10, wherein said recombinant baculovirus is an *Autographa californica* baculovirus.

13. The recombinant protein enhancin encoded by said recombinant baculovirus expression vector of claim 10.

14. The composition of claim 9, wherein the said second material is a nuclear polyhedrosis virus.

* * * * *